United States Patent [19]

Briggs et al.

[11] 3,932,943

[45] Jan. 20, 1976

[54] METHOD OF PREPARATION OF LYOPHILIZED BIOLOGICAL PRODUCTS

[75] Inventors: Anglis R. Briggs, Newark, Del.; Thomas J. Maxwell, Philadelphia, Pa.

[73] Assignee: E. I. Du Pont de Nemours and Company, Wilmington, Del.

[22] Filed: Aug. 16, 1974

[21] Appl. No.: 498,326

Related U.S. Application Data

[60] Division of Ser. No. 340,196, March 12, 1973, which is a continuation-in-part of Ser. No. 177,834, Sept. 3, 1971, abandoned, and a continuation-in-part of Ser. No. 63,942, Aug. 14, 1970, Pat. No. 3,721,725.

[52] U.S. Cl. .................................................. 34/5
[51] Int. Cl.² ........................................ F26B 5/06
[58] Field of Search .............................. 34/5, 92

[56] References Cited
UNITED STATES PATENTS

| | | | |
|---|---|---|---|
| 2,149,304 | 3/1939 | Masucci | 424/85 |
| 3,228,838 | 1/1966 | Rinfret et al. | 34/5 |
| 3,269,025 | 8/1966 | Dryden et al. | 34/5 |
| 3,281,950 | 11/1966 | Kautz | 34/5 |
| 3,607,858 | 9/1971 | Querry et al. | 34/5 |
| 3,620,776 | 11/1971 | Mishkin | 34/5 |
| 3,888,017 | 6/1975 | McBride | 34/5 |

*Primary Examiner*—John J. Camby

[57] ABSTRACT

Disclosed herein is a homogeneous, lyophilized particulate product of a substance containing at least one biologically active component and a process for its preparation which involves forming a solution or colloidal suspension of the substance, spraying the solution or colloidal suspension into a moving bath of fluorocarbon refrigerant and lyophilizing the resultant frozen droplets. The porous product has a spherical shape, free-flowing properties, and rapid dissolution times.

21 Claims, No Drawings

METHOD OF PREPARATION OF LYOPHILIZED BIOLOGICAL PRODUCTS

CROSS REFERENCE TO RELATED APPLICATIONS

This is a divisional of application Ser. No. 340,196, filed on Mar. 12, 1973, which in turn is a continuation-in-part of application Ser. No. 177,834, filed Sept. 3, 1971, now abandoned, and also of application Ser. No. 63,942, filed on Aug. 14, 1970, which issued as U.S. Pat. No. 3,721,725 on Mar. 20, 1973.

BACKGROUND OF THE INVENTION

This application relates to a novel lyophilized product and to a process for its preparation. More specifically, it relates to a lyophilized form of a substance having at least one biologically active component.

Biologically active products, including: pharmaceuticals such as vitamins, hormones, tranquilizers and antibiotics; proteins such as enzymes and gelatins; and control products such as plasma or serum are in wide spread use. Despite this fact, there are still many problems with the way in which they are produced and the form in which they are provided. For example, since they are biologically active, they should be provided in a form which will preserve their biological activity for a reasonable time. One method of accomplishing this is to freeze the substance and retain it in its frozen state. This, however, entails the extra handling and equipment necessary to keep the substance frozen at all times.

Alternatively, quantities of the substance have been frozen in bulk and subsequently lyophilized. The product no longer has to be maintained below freezing, but the slow freezing that takes place during bulk freezing creates other problems. For one thing, slow freezing promotes the development of concentration gradients. When blood serum or plasma is frozen slowly, for example, the cholesterol and triglyceride globules within the serum or plasma are forced to coalesce. These globules, upon dissolution of the lyophilized product in an aqueous solvent, apparently do not redisperse but remain coalesced. The result is a non-uniform product.

Another problem that slow freezing produces is degradation of the various biological constituents. Freezing of enzyme solutions, for example, generally appears to have a degradative effect upon the enzymes. The slow freezing that takes place when bulk freezing is used and the concentration gradients that build up in such products merely increase this degradation. One effort to counteract the enzyme degradation resulting from the slow freezing of a plasma, for example, has been to entirely remove the enzyme and other constituents from the plasma and to weigh in predetermined quantities of these substances to achieve constant level after the product is frozen and dried. The weight of an enzyme, however, does not truly represent the amount of material that should be added. As enzymes are subject to degradation, the true measure of enzyme concentration is activity, for which weight is not an accurate substitution.

Finally, the reconstitution of lyophilized substances by dissolution in water meets with difficulties when the substance is frozen in bulk form. Such reconstitution often requires upwards of 20 to 30 minutes and often results in a lack of clarity. This is a particularly bothersome problem with control products, such as serum or plasma, when subsequent photometric analysis is performed on them. Furthermore, when the products are frozen in bulk form, they are difficult to dispense in any other form but the reconstituted form.

SUMMARY OF THE INVENTION

The present invention provides a method of overcoming the deficiencies which have been described above by providing a process for making a homogeneous lyophilized product of a substance containing at least one biologically active component which comprises the steps of a. forming a solution, or a colloidal suspension, of the substance in a liquid which will freeze and which will also vaporize at a temperature which will not destroy the biological activity of the material;

b. spraying the solution or colloidal suspension in the form of droplets into a moving bath of boiling fluorocarbon refrigerant having a temperature of below about $-20\,°C.$, whereby the droplets are frozen;

c. subjecting the frozen droplets to a vacuum;

d. thereafter, while maintaining the vacuum, subjecting said droplets to a temperature such that essentially all of the liquid in the droplets sublimes and forms particles from said droplets; and e. allowing the particles to come to room temperature and pressure.

The substance is usually injected into the fluorocarbon refrigerant in the form of an aqueous solution, but any solution formed with the liquid which will freeze and which will also vaporize at a temperature which will not destroy the biological activity of the material can be used. For example, organic liquids such as dioxane or mixtures of water with organic liquids such as ethanol can be used. Furthermore, the substance need not be introduced into the fluorocarbon refrigerant in the form of a solution; a colloidal suspension may also be used. For convenience, however, the remaining discussion will be limited to aqueous solutions.

There may be more than one biologically active component in the substance. Serum or plasma, for example, contains a variety of biologically active components. In itself, it will contain enzymes, vitamins, hormones, and under certain circumstances, a variety of antibiotics and even tranquilizers. In the context of this invention, the term biologically active means that the component retains its biological properties. In addition to the biologically active components, the substance may contain other inert materials, such as bulking agents. The present invention, therefore, contemplates the blending of a number of biological products and the blending of biological products with inert fillers. Due to the fact that the blending occurs in solution, and the fact that the particles are a homogeneous representation of the constituents of the solution, the present invention provides a process by which accurate blending of the various ingredients can be produced.

The biologically active component in the substance may be a pharmaceutical, a protein, a control product or any other biologically active material. Pharmaceuticals include: vitamins, such as Vitamin C; hormones, such as testosterone; tranquilizers, such as chlorpromazine; and antibiotics, such as bacitracin, penicillin, polymyxin B and tetracycline. Proteins include gelatins and enzymes, such as maltase. A variety of control products such as serum or plasma, hemoglobin and cholesterol can also be produced.

The solution is sprayed into a moving bath of boiling fluorocarbon refrigerant having a temperature below about −20°C. The spraying is conducted from a sufficient height above the refrigerant so that droplets of the solution are formed. Spraying the solution into the boiling fluorocarbon refrigerant in the form of droplets achieves rapid freezing. The droplet form presents a large surface area in the cold environment and hence promotes rapid freezing.

The size of the particles after lyophilization is a function of the size of the droplets formed while spraying the solution into the refrigerant. Preferably, the solution is sprayed through 16 to 28 gauge needles. Using a needle smaller than 28 gauge results in particles sufficiently small that electrostatic effects tend to interfere with their ease of handling. Using a needle with a gauge larger than 16 produces sufficiently large particles that they tend to fracture, which may reduce their free flowing and ease of handling. Additionally, product homogeneity is better assured if the particles are not fractured. Concentration gradient caused by freezing will also develop within each particle. Having unfractured particles eliminates the dehomogenizing effects of any concentration gradient that does develop during the freezing step.

The use of fluorocarbon refrigerants is critical. In the first place, the density of fluorocarbon refrigerants is such that the frozen droplets float on the refrigerant. If liquid nitrogen is used, for example, the droplets have a tendency to sink to the bottom of the refrigerant and tend to agglomerate. The fact that the particles float, tends to prevent this and also allows the particle to be removed by a size from the top of the refrigerant.

Also fluorocarbon refrigerants generally have a higher boiling point than other liquid refrigerants, for example, liquid nitrogen. The higher boiling point, being closer to the temperature of the solution droplets, results in less of a vapor phase barrier between the particle and the refrigerant. This permits more rapid freezing of the particles than can be achieved with even colder refrigerants such as liquid nitrogen. This fast freezing also prevents the loss of those constituents of the solution that would otherwise be soluble in the fluorocarbon. Thus, when the product is serum or plasma, for example, negligible loss of cholesterol and triglycerides has been found even though these are organic compounds that are normally soluble in the fluorocarbon. Specifically, with a lower detection limit of 2 to 3 percent, no loss of these substances has been found. Furthermore, the use of the fluorocarbon refrigerant produces particles that are spherical in shape, whereas the use of liquid nitrogen produces less spherical and less uniform sized particles. The use of fluorocarbon refrigerant, therefore, is to be preferred over the use of other colder refrigerants such as liquid nitrogen.

Of the various fluorocarbon refrigerants (which E. I. du Pont de Nemours and Company of Wilmington, Del. sells under the tradename "Freon") dichlorodifluoromethane (Freon 12) represents a preferred example. This refrigerant boils at about −25°C. Imparting a slight motion to the fluorocarbon refrigerant as the solution is sprayed into it will separate the freezing particles and prevent their agglutination.

After freezing, the solidly frozen particles are lyophilized; care being taken to prevent any intervening thawing. Lyophilization is accomplished by subjecting the particles, while frozen, to a vacuum and thereafter supplying sufficient heat to compensate for the heat of sublimation. Since the particles are under a vacuum, the temperature of the environment may be raised to a point which would cause the particles to thaw under atmospheric pressure. At 50 to 70$\mu$ Hg., for example, the particles may be exposed to a shelf temperature of 120°F. for a short while to begin the lyophilization, and then allowed to equilibrate to room temperature to avoid heat denaturation. Sublimation should continue until the particles are dry. Preferably the product temperature should be below about 37°F.

After sublimation the particles are brought to room temperature and pressure. Portions of the particles are then removed as convenient.

In addition to promoting rapid freezing, the particulate nature of the product appears to be partially responsible for its fast dissolution time. Its porous nature also contributes to this. Furthermore, the resultant particulate product has a high homogeneity, which permits it to be apportioned by the expedient method of measuring out amounts of the dry product. The low bulk density and free flowing properties of the product permit measuring out by either weight or volumetric means, with particular advantage in the dry volumetric measurement. The homogeneous product of the slow freezing method of the prior art cannot be weighed out after lyophilization, but rather must be volumetrically apportioned prior to freezing.

The operation and advantages of the present invention will now be discussed with reference to serum or plasma. Because serum or plasma is a composite substance which contains a plurality of biologically active components, including enzymes, hormones, vitamins, etc., a detailed discussion of this substance and the way in which each component is preserved will provide the basis for a full understanding of the invention.

Serum and plasma represent the remnants of blood after the particulate material has been separated from it, often by centrifuging. For plasma, an anticlotting agent, usually sodium citrate, is added to the fresh blood immediately upon its obtention to prevent the precipitation of fibrinogen, which thus forms one constituent of plasma. To obtain serum, no such anticlotting agent is added, fibrinogen precipitates, and it is removed during the separation step along with the cellular material. Because of its close chemical and physical similarity to samples undergoing actual testing, serum or plasma of known content is used as a standard or control in clinical analysis. Preserved serum or plasma can also be used in other applications, such as vaccine, gammaglobulin preparations and special antibodies or antigenic substances.

When produced by the present method, the rapid freezing of the serum or plasma results in greater activity retention and stability of the enzymes and other biological substances within the serum or plasma. The rapid freezing also prevents the build up of large ice crystals and produces an even distribution of biologically active components throughout the frozen particle. The homogeneous size and distribution of crystalline regions of water and hence the small size and even distribution of the pores which form when the particles are lyophilized, also appears to aid in short dissolution times when the particles are dissolved. Dissolution times of 20 to 30 seconds have been observed as compared to 20 or 30 minutes of the prior art. Finally, the rapid freezing results in a lyophilized product with greater clarity upon subsequent dissolution.

Prior to freezing, various other ingredients may be added to or taken from the serum or plasma. In particular, an ingredient may be added to control the pH which the final lyophilized product will obtain when dissolved in a neutral aqueous solvent. This is especially important because lyophilization removes indeterminate amounts of $CO_2$ and thus raises the pH of the final product when dissolved. The amount of the acidic ingredient to be added is determined by taking small amounts of the serum before its freezing, adding differing quantities of acid to each, freezing and lyophilizing them, dissolving them in water, and determining the pH of each. Using at least three such solutions gives a calibration curve of the amount of acid that must be added to the serum or plasma before freezing to give the desired pH upon dissolution of the final lyophilized product. The final pH should generally lie in the range of 6.8 to 7.4.

The resulting product consists of free flowing spheres having at least 90 percent pores and preferably not exceeding about 1 mm. in diameter. With the exception of $CO_2$ each of the particles is composed of the constituents of serum or plasma in the proportions in which they existed in the original fluid. Furthermore, because of the fast freezing, each of the spheres generally is homogeneous throughout. The Standard Dissolution Time for the particles, as determined by the test method detailed in Example II, does not exceed 2 minutes.

Because of the invariability of the product's composition from particle to particle, the product may be weighed out into portions of a desired size or may be dispersed as a free flowing powder using a volumetric solids dispersion. This weighing of a dry product is more convenient and has less attendant errors than volumetric measurements of liquid.

In one method of apportioning the product by weight, portions having the desired amount of a particular constituent are removed from the mass of lyophilized particles. Since the ratios of most of the various constituents within the serum or plasma remain generally unaltered during the lyophilization procedure, insuring that a portion withdrawn from the mass contains a predetermined amount of a particular constituent generally insures that that portion will contain specific amounts of most of the other constituents of the serum or plasma. In particular, if the size of the portion is selected so that, upon dissolution in a recommended amount of water, the concentration of a particular constituent will match that in the original serum or plasma, the concentration of the other constituents within the serum or plasma will also be found to be close to that of the original.

Sodium is one constituent that may be used to determine the size of the portions removed. Sodium has the particular benefit that it remains unaffected by lyophilization, and does not deactivate under various conditions as do enzymes. In general, the normal concentration of sodium within serum or plasma is approximately 140 milliequivalents per liter. Thus, portions should be selected that upon dissolution in the proper amount of water, will give sodium concentrations approximating that above, the range of 135 to 143 milliequivalents per liter being acceptable.

A convenient and accurate method for the determination of sodium is flame photometry. A small amount of the lyophilized particles is analyzed for its sodium content per unit weight. These results then determine the weight of the lyophilized particles to be removed in order to give the predetermined amount of sodium within each portion. When abnormal concentrations of constituents are desired, portions having greater or less weight of sodium (or any other particular constituent) can be removed from the mass.

Lyophilization, however, causes the loss of part of the dissolved carbon dioxide within the serum or plasma. This raises the pH of the final product when dissolved in distilled water to an abnormally high level. Another deleterious result of the loss of $CO_2$ and its concomitant pH elevation is the loss of constituents that are pH sensitive. One such constituent is glutamic pyruvate transaminase (GPT).

One method to counteract this loss of carbon dioxide would be to add sufficient acid to the serum or plasma solution before freezing to bring this solution's pH up to a predetermined level. The difficulty with this method, however, lies in the fact that the exact amount of carbon dioxide lost upon lyophilization varies from batch to batch of serum. Thus, this method will not result in various batches achieving a uniform pH upon dissolution.

Alternatively, prior to freezing, differing quantities of acid may be added to several aliquots of the serum or plasma. These aliquots, with the added acid, may then be lyophilized (e.g., by conventional techniques), reconstituted in water, and each aliquot analyzed for its pH. This gives a standard curve of pH versus quantity of acid added to the original serum or plasma. This curve then shows the correct amount of acid that must be added so that the lyophilized product will have the correct pH.

A suitable acid to accomplish this purpose is 4N citric acid. Generally, 20 to 23 milliequivalents of acid per liter of serum or plasma results in the final product having the desired pH of 6.8 to 7.4 upon dissolution in distilled water. Additionally, prior to freezing, other ingredients may be added to or subtracted from the serum or plasma solution to give a desired effect in the particular case. In adding the acid, the pH of the solution should not be allowed to drop below approximately 6.0; lower pH's approach the isoelectric point of the proteins within the serum. This would cause the proteins to precipitate out of the solution and deleteriously affect the final results. Generally, however, the amount of $CO_2$ lost upon lyophilization would not require adding a large enough quantity of acid to cause the pH to drop below 6.0.

EXAMPLE I

To three 50 ml. aliquots of fresh serum were added 288 $\mu$l, 325 $\mu$l, and 350 $\mu$l of 4N citric acid. These aliquots were frozen (in bulk) and lyophilized under 100$\mu$ Hg. or less at ambient temperatures. The lyophilized residues from the aliquots were macerated. Five hundred milligrams of each of the three macerated residues upon dissolution in 5 ml. distilled water gave pH's of 7.5, 7.4 and 7.25, respectively, indicating that adding 7.0 ml. of 4N citric acid per liter of serum would result in a pH of 7.25 upon dissolution of the product in distilled water. Accordingly, this amount of citric acid was added to the serum.

The serum was then sprayed from 26 gauge needles at 15 to 20 psi into moving boiling dichlorodifluoromethane refrigerant having a temperature of about $-25°C$.

The frozen droplets were continuously collected with a 80 mesh sieve and placed into ceramic pans to a depth not exceeding one inch and subjected to vacuum of about 50 to 70 µHg. at an environmental temperature of 120°F. at the beginning which is thereafter allowed to equilibriate to room temperature.

Samples of 420, 440 and 493 mg. of the lyophilized particles were reconstituted with 5 ml. of distilled water and analyzed for sodium content by flame photometry and were found to contain 124, 131, 140 meq./liter, respectively. The original serum contained 140 meq./liter of sodium. Accordingly 493 mg. portions of the particles were removed and placed in vials to be reconstituted with 5 ml. distilled water. The particles were refrigerated at about 5°C. until reconstitution.

One such portion of the lyophilized product was reconstituted and analyzed for various constituents. Table I gives the results for tests performed upon the original serum ("Orig.") and the freeze-sprayed serum of the present invention ("F.S."). The test designation is as follows.

LDH — Lactic dehydrogenase
PCHE — Pseudocholinesterase
GPT — Glutamic Pyruvate Transaminase
GOT — Aspartate Aminotransferase
CPK — Creatine Phosphokinase
ALK.P — Alkaline Phosphatase
T.P. — Total Proteins
BUN — Blood Urea Nitrogen Most constituents generally lost little, if any, activity through the process. The standard deviations, where obtained, were about that for the original serum, being better in the instances of GPT, and CPK, and slightly worse for Glucose.

mm. inside length, i.e., from vial bottom to inside surface of the sealing rubber stopper. While in unstoppered vials A and B the blood serum was conventionally frozen and lyophilized. The resulting cake-like product approximated the shape of the bottom portion of the vial. The weight of lyophilized serum in each A and B vial was 500 ± 5 mg. The lyophilized serum in vial B was macerated or finely comminuted by breaking the cake up with a spatula while in the vial. Vials A and B were stoppered and stored at 4° to 10°C.

Part C was freeze-sprayed and lyophilized according to the procedure of Example I. The resulting Product C consisted of spherical, highly porous, free-flowing particles all of which passed through a U.S. Standard 20 mesh sieve; accordingly, the particles did not exceed 840 microns (0.84 mm.) in diameter. Portions of Product C each weighing 500 mg. were introduced into glass vials described above, which were then stoppered and stored at 4° to 10°C.

Comparative Standard Dissolution Times for Products A, B, and C were determined according to the following procedure. Five-milliliter portions of deionized water (R ≥ 1 megohm) at 25 ± 2°C. were quickly introduced into each of a series of vials from groups A, B and C which had previously been permitted to equilibrate at the same temperature. An automatic pipetting device introduced this water while the dispensing tip of the pipette was held in contact with the inside wall surface of each vial. Each vial was then quickly stoppered and placed on an electrically driven roller mill with the cylindrical axis of the vial horizontal. Elapsed time from introduction of water to placing on the mill did not exceed about 5 seconds. The rollers of the mill were rotating at a speed designed to rotate the vials at

TABLE 1

| CONSTITUENT | MEAN | STD. DEVIATION | N | METHOD REF. |
|---|---|---|---|---|
| Glucose - Orig. | 93.1 mg/dl | 1.58 | 5 | F. H. Schmidt, Klin. Wschr. 40, |
| F.S. | 89.3 | 4.87 | | 585 (1961) |
| LDH - Orig. | 153 uts. | 4.76 | 4 | W. E. C. Wacker et al, New England, |
| F.S. | 127 | 3.41 | | J. Med. 255 449 (1956) |
| PCHE - Orig. | 12.32 uts | 0.39 | 5 | E. H. Gal et.al, Clin. Chem. Acta. |
| F.S. | 11.98 | 0.41 | | 2 316 (1957) |
| GPT - Orig. | 12.8 uts. | 2.95 | 5 | H. Bergmeyer et al, Methods of Ens. |
| F.S. | 9.2 | 0.45 | | Analysis, H. Bergmeyer Ed. pp. 848–853, Academic Press (New York, 1965) |
| GOT - Orig. | 31.2 uts | 1.92 | 5 | A. J. Karmen, Clin. Invest. 34, |
| F.S. | 24 | 2.0 | | 131 (1955) |
| CPK - Orig. | 73.6 uts. | 2.96 | 5 | J. W. Hess et.al, Amer. J. Clin. Path |
| F.S. | 56 | 1.41 | | 50, 89 (1968) |
| ALK.P - Orig. | 9.4 uts/dl | 3.79 | 5 | O. A. Bessey et al, J. Biol. Chem. |
| F.S. | 5.9 | 0.77 | | 164, 321 (1946) |
| Albumin - Orig. | 4.32 g/dl | 0.012 | 5 | B. T. Doumas et.al, Clin. Chem. Acta. |
| F.S. | 4.5 g/dl | 0.007 | | 31, 87 (1971) |
| T.P. - Orig. | 7.38 g/dl | 0.028 | 5 | G. R. Kingsley, J. Biol. Chem. 131, |
| F.S. | 7.20 g/dl | 0.038 | | 197 (1939) |
| BUN - Orig. | 19.2 uts. | 0.28 | 5 | R. Nadeau, U.S. Patent No. 3,485,723 |
| F.S. | 18.75 uts. | 0.09 | | |

The turbidity increase was measured both for conventional and the present freeze-spray lyophilizations. The particulate product of the freeze-spray method displayed less than 20 percent of the increase in turbidity observed for the product of conventional lyophilization.

EXAMPLE II

Blood serum was compensated to a pH of 7.4 by the addition of 6.25 ml. of 4N citric acid per liter of serum. This pH-compensated blood serum was divided into parts A, B, and C. A number of 5.3 ml. portions of parts A and B were introduced into a flat bottomed cylindrical glass vial measuring 20 mm. inside diameter and 30

32 revolutions per minute. To obtain the dissolution rates vials were removed from the mill at selected time intervals. The stopper on each of the vials was quickly removed and a sampling pipette removed a 100 µ l. liquid sample which was analyzed for total protein by the colorimetric assay described by H. L. Rosenthal and H. T. Cundiff in CLINICAL CHEMISTRY, 2, 394 (1956). Standard Dissolution Times of Products A, B, and C, reported below, were determined from a plot of percent dissolution vs. elapsed time on the roller mill. One-hundred percent (100 percent) dissolution corresponds to an assay of 7 gms. of protein per 100 ml. of blood serum.

| Product | Standard Dissolution Time, seconds |
|---------|-----------------------------------|
| A | 1200 |
| B | 1200 |
| C | 90 |

By visual comparison, the solutions obtained by completely reconstituting Products A and B exhibited considerably greater tubidity than did the solution obtained by completely reconstituting Product C.

EXAMPLE III

A 25% (w/v) solution of bacitracin was prepared in high purity distilled water. This solution was injected into rapidly moving, boiling Freon, at a temperature of −25° C., through a 27 gauge needle at 80 psi. The injection rate was 8 ml./min. The needle was maintained at a distance of 25 cm. from the surface of the Freon.

The frozen droplets were collected with a sieve and placed in a Teflon lined stainless steel pan. The frozen droplets were subjected to vacuum of about 20 microns Hg. with the environment at room temperature for a period of 10 hours to carry out sublimation of the water. A plurality of spherical particles was produced. The dry particles were collected and stored in vials at 4°C.

EXAMPLE IV

A 10% (w/v) solution of polymyxin B was prepared in high purity distilled water. This solution was injected into rapidly moving, boiling Freon, at a temperature of −25°C., through a 26 gauge needle at 22 psi. The injection rate was 11 ml./min. The needle was maintained at a distance of 10 cm. from the surface of the Freon.

The frozen droplets were collectd with a sieve and placed in a Teflon lined stainless steel pan. The frozen droplets were subjected to vacuum of about 20 microns Hg. with the environment at room temperature for a period of 10 hours to carry out sublimation of the water. A plurality of spherical particles was produced. The dry particles were collected and stored in vials at 4°C.

EXAMPLE V

A saturated solution of tetracycline was prepared by addition of 50 gm. of tetracycline to 500 ml. of high purity distilled water and mixing the suspension for a period of one half to three fourths hours. The mixture was filtered to remove the undissolved tetracycline which amounted to about 10 gm. The resultant solution was about 8 percent (w/v) in tetracycline.

The tetracycline solution was injected into rapidly moving, boiling Freon, at a temperature of −25°C., through a 26 gauge needle at 30 psi. The injection rate was 17 ml/min. from a distance of 18 cm. above the surface of the Freon.

The frozen droplets were collected with a sieve and placed in a Teflon lined aluminum pan. The frozen droplets were subjected a vacuum of 10 microns Hg. over a 17 hour period to effect sublimation of the water. Shelf temperature in the sublimation was −25°C. at the beginning of the process and increased to +37°C. at 1½ hours. The +37°C. temperature was maintained throughout the remaining 15½ hour sublimation period. A plurality of spherical particles was produced. The dry particles were placed in vials and stored at 4°C.

EXAMPLE VI 2.5 gm. of chlorpromazine was dissolved in 10 ml. of high purity distilled water. The solution was injected into rapidly moving, boiling Freon, at a temperature of −25°C., using a 5 ml. syringe fitted with a 28 gauge needle. The syringe was held 23 cm. above the surface of the Freon and the injection rate maintained at about 5 ml./min.

The frozen droplets of chlorpromazine were collected with a sieve and placed in a Teflon lined stainless steel pan. The frozen droplets were subjected to a vacuum of about 20 microns Hg. with the environment at room temperature for a period of 10 hours to effect sublimation of the water. A plurality of dry particles was produced. The dry particles were collected and stored in vials at 4°C.

EXAMPLE VII

Eighty ml. of a solution containing 9% of inositol and 18% (w/v) of mannitol was mixed with 20 ml. of maltase enzyme. This solution was injected into rapidly moving, boiling Freon at a temperature of −25°C., through a 26 gauge needle at 35 psi. The injection rate was 20 ml./min. The needle was maintained at a distance of 18 cm. from the surface of the Freon.

The frozen droplets were collected with a sieve and placed in a Teflon lined stainless steel pan. The frozen droplets were subjected to vacuum of about 20 microns Hg. with the environment at room temperature for a period of 10 hours to carry out sublimation of the water. A plurality of spherical particles was produced. The dry particles were collected and stored in vials at 4°C.

EXAMPLE VIII

To 250 ml. of a 5% (w/v) aqueous solution of sodium monoglutamate, 50 mg. of testosterone was added. This solution was injected into rapidly moving, boiling Freon at a temperature of −25°C., through a 26 gauge needle at 10 psi. The injection rate was 10 ml./min. The needle was maintained at a distance of 10 cm. from the surface of the Freon.

The frozen droplets were collected with a sieve and placed in a Teflon lined stainless steel pan. The frozen droplets were subjected to a vacuum of about 20 microns Hg. with the environment at room temperature for a period of 10 hours to carry out sublimation of the water. A plurality of spherical particles was produced. The dry particles were collected and stored in vials at 4°C.

EXAMPLE IX

A 10% (w/v) aqueous solution of Vitamin C containing 10 grams (w/v) of inositol was prepared. This solution was injected into rapidly moving, boiling Freon at a temperature of −25°C., through a 26 gauge needle at 20 psi. The injection rate was 16 ml./min. The needle was maintained at a distance of 10 cm. from the surface of the Freon.

The frozen droplets were collected with a sieve and placed in a Teflon lined stainless steel pan. The frozen droplets were subjected to a vacuum of about 50 microns Hg. with the environment at room temperature for a period of about 48 hours to carry out sublimation of the water. A plurality of spherical particles was produced.

EXAMPLE X

Red blood cells, washed with 0.85 percent sodium chloride, were hemolyzed by freezing and thawing, and then centrifuged to remove debris. The supernatent was injected into rapidly moving, boiling Freon at a temperature of −25°C. through a 26 gauge needle maintained at a distance of about 18 cm. from the surface of the Freon. The frozen droplets were collected with a sieve and placed in a Teflon lined stainless steel pan. The frozen droplets were subjected to a vacuum of about 20 microns Hg. with the environment at room temperature for a period of 10 hours to carry out sublimation of water. A plurality of spherical particles was produced. The dry particles were collected and stored in vials at 4°C.

EXAMPLE XI

A solution was made by dissolving 14 gm. of cholesterol in 60 ml. of 94% ethanol containing 2% sodium lauryl sulfate at 75°–90°C. A 2% (w/v) aqueous sodium lauryl sulfate solution was prepared. With stirring, 30 ml. of the cholesterol solution were added to 100 ml. of the aqueous sodium lauryl sulfate solution to form a colloidal suspension. This colloidal suspension was injected into rapidly moving, boiling Freon at a temperature of −25°C. through a 26 gauge needle at 20 psi. The injection rate was 12 ml./min. The needle was maintained at a distance of 17 cm. on the surface of the Freon.

The frozen droplets were collected with a sieve and placed in a Teflon lined stainless steel pan. The frozen droplets were subjected to a vacuum of about 20 microns Hg. with the environment at room temperature for a period of 20 hours to carry out sublimation of the water. A plurality of spherical particles was produced. The dry particles were collected and stored in vials at 4°C.

EXAMPLE XII

A 1 percent solution (w/v) of gelatin (USP) was prepared in pure distilled water. The temperature of the solution was 45°–50°C. The solution was injected into rapidly moving boiling Freon, at a temperature of −25°C., through a 24 gauge needle at 100 psi. The injection rate was 10 ml./min. The needle was maintained at a distance of 10 cm. from the surface of the Freon.

The frozen droplets were collected with a sieve and placed in a Teflon lined stainless steel pan. The frozen droplets were subjected to a vacuum of about 50 microns with the environment at room temperature for a period of about 17 hours to carry out sublimation of the water. A plurality of spherical particles was produced. The dry particles were collected and stored in vials at 4°C.

What is claimed is:

1. A method of making a homogeneous lyophilized product of a substance containing at least one biologically active component which comprises:
    a. forming a solution or colloidal suspension of said substance in a liquid which will freeze and which will also vaporize at a temperature which will not destroy the biological activity of said material;
    b. spraying said solution or colloidal suspension, onto the surface of a moving bath of boiling fluorocarbon refrigerant having a temperature of below about −20°C. from a sufficient height above the surface of the moving bath to allow droplet formation before the solution or suspension strikes the surface of the moving bath, whereby said droplets are frozen; and
    c. lyophilizing said droplets to form a plurality of uniform sized porous spheres.

2. The method of claim 1 wherein said liquid comprises an organic liquid.

3. The method of claim 1 wherein said liquid is water.

4. A method of making a homogeneous lyophilized product of a substance which is soluble in water and which contains at least one biologically active component which comprises:
    a. forming an aqueous solution of said substance;
    b. spraying said solution onto the surface of a moving bath of boiling fluorocarbon refrigerant having a temperature of below about −20°C. from a sufficient height above the surface of the moving bath to allow droplet formation before the solution strikes the surface of the moving bath, whereby said droplets are frozen; and
    c. lyophilizing said droplets to form a plurality of uniform sized porous spheres.

5. The method of claim 4 wherein said substance comprises a pharmaceutical.

6. The method of claim 4 wherein said substance comprises a pharmaceutical selected from the group consisting of vitamins, hormones, tranquilizers and antibiotics.

7. The method of claim 4 wherein said substance comprises a protein.

8. The method of claim 7 wherein said substance comprises an enzyme.

9. The method of claim 7 wherein said substance comprises a gelatin.

10. The method of claim 4 wherein said substance comprises a control product.

11. The method of claim 4 wherein said substance comprises serum or plasma.

12. The method of claim 4 wherein said fluorocarbon refrigerant is dichlorodifluoromethane.

13. A method of making a homogeneous lyophilized product of serum or plasma which comprises:
    a. spraying a solution of serum or plasma onto the surface of a moving bath of boiling fluorocarbon refrigerant having a temperature below about −20°C. from a sufficient height above the surface of the moving bath to allow droplet formation before the solution strikes the surface of the moving bath, whereby said droplets are frozen; and
    b. lyophilizing said droplets to form a plurality of uniform sized porous spheres.

14. The method of claim 13 wherein prior to spraying, there is added an amount of at least one substance that will affect the pH of said particles of said portion upon dissolution in an aqueous solvent.

15. The method of claim 14 wherein said amount of said substance is such that said particles upon dissolution in a neutral aqueous solvent will result in a solution having a pH of about 6.8 to 7.4.

16. The method of claim 15 wherein about 20 to 23 milliequivalents of citric acid is added per liter of serum or plasma.

17. The method of claim 13 wherein the size of said portion removed contains a predetermined amount of a specific constituent therein.

18. The method of claim 13 wherein removing said portion is performed by weighing out a predetermined weight of said particles.

19. The method of claim 13 wherein removing said portion is performed by measuring out a predetermined volume of said particles.

20. The method of claim 13 wherein said fluorocarbon refrigerant is dichlorodifluoromethane.

21. A method of making a homogeneous lyophilized product of serum or plasma which comprises:
   a. adding to the serum or plasma solution a quantity of citric acid which will result in the lyophilized product having a pH of from 6.8 to 7.4 upon dissolution in a substantially neutral aqueous solvent;
   b. thereafter spraying said serum or plasma solution onto the surface of a moving bath of boiling fluorocarbon refrigerant having the temperature below about −20°C. from a sufficient height above the surface of the moving bath to allow droplet formation before the solution strikes the surface of the moving bath, whereby said droplets are frozen;
   c. lyophilizing said droplets to form a plurality of uniform sized porous spheres, and
   d. weighing out to a predetermined weight at least one portion of said particles, said portion of said predetermined weight containing a predetermined amount of sodium.

* * * * *